United States Patent [19]
Sherwin et al.

[11] Patent Number: 5,670,148
[45] Date of Patent: Sep. 23, 1997

[54] COMBINED CELLULAR AND IMMUNOSUPPRESSIVE THERAPIES

[75] Inventors: Stephen A. Sherwin, San Francisco; Robert B. Dubridge, Belmont, both of Calif.

[73] Assignee: Cell Genesys, Inc., Foster City, Calif.

[21] Appl. No.: 314,452

[22] Filed: Sep. 28, 1994

Related U.S. Application Data

[63] Continuation of Ser. No. 781,075, Oct. 21, 1991, abandoned.

[51] Int. Cl.$^6$ .......................... C12N 15/00; A01N 63/00; A61K 35/12
[52] U.S. Cl. .................... 424/93.21; 435/192.3; 424/933; 424/937; 424/572
[58] Field of Search ............................... 424/93.1

[56] References Cited

U.S. PATENT DOCUMENTS 4,980,286  12/1990  Morgan ......................... 435/172.3
5,175,004  12/1992  Matsumura ..................... 424/520

OTHER PUBLICATIONS

E. Alamartine et al., "The influence of prophylactic immunosuppressive regimens on natural killer and lymphokine-activated killer cells in renal transplant recipients", *Transplantation*, 50:969–973 (1990).

M. Bix et al., "Rejection of class I MHC deficient haemapooietic cells by irradiated MHC–matched mice", *Nature*, 349:329–331 (1991).

Dupuy et al, "Cyclosporine A inhibits the antigen-presenting functions of freshly isolated human hangerhans cells in vitro", *J. Inves. Dermatology*, 96(4):408–413 (1991).

Kosugi and Shearer, "Effect of cyclosporine A on lymphopoiesis", *J. Immunol.*, 146:1416–1421 (1991).

N. Liao et al., "MHC class I deficiency: susceptibility to natural killer (NK) cells and impaired NK activity", *Science*, 253:199–202 (1991).

C. Ohlen et al, "Prevention of allogeneic bone marrow graft rejection by H-2 transgene in donor mice", *Science*, 246:666–668 (1989).

*Primary Examiner*—Suzanne E. Ziska
*Attorney, Agent, or Firm*—Pamela J. Sherwood; Fish & Richardson P.C.

[57] ABSTRACT

Novel regimens are provided for administering foreign genetically modified allogeneic cells to a host by combining the administration of the cells with a reduced regimen of an immunosuppressive agent. Particularly, cells having a reduced level of Class I MHC antigens may be employed in a variety of cellular therapy situations, where foreign cells are engrafted to treat diseased states.

6 Claims, No Drawings

COMBINED CELLULAR AND IMMUNOSUPPRESSIVE THERAPIES

This is a continuation of application Ser. No. 07/781,075 filed Oct. 21, 1991, now abandoned.

INTRODUCTION

1. Technical Field

The field of this invention is cellular transplantation therapy.

2. Background

There are many medical conditions arising from the loss of cell number or function where cellular therapies could be employed. These therapies may involve employment of autologous or allogeneic cells or tissue, and even instances of xenogeneic cells or tissue. Such cellular therapies, including bone marrow transplantation, organ transplants or grafts, skin grafts, muscle transplants, blood transfusions or particular blood cell populations, e.g., white blood cells and platelets, endocrine tissue, islet cells, e.g., islets of Langerhans, adrenal cells, hepatic cells, retinal epithelial cells, endothelial cells, osteoblasts, keratinocytes, chondrocytes and the like, involve the administering of cells or tissue to a mammalian host, where the cells are to remain viable and functional, usually substituting for or interdigitating with the diseased or incompetent cells or tissue of the host. Similarly, cellular transplant therapies may be employed for a variety of purposes using cells modified in a variety of ways: cells altered to reduce immunogenicity; cells altered to produce therapeutic compounds, either naturally occurring or mutated, such as cytokines, hormones, clotting factors, anti-clotting factors, growth hormones, colony stimulating factors interferons, immunosuppressants, etc.; cells altered to be resistant to infection with microorganisms, viruses or other pathogens; and cells altered to be capable of homing to targeted sites of malignant or infectious disease processes.

As is well known, the immune system protects a host from foreign substances. The immune system is able to detect the introduction of allogeneic tissue by virtue of the major histocompatibtlity complex antigens. These antigens comprise for the most part Class I and II MHC, although there are minor histocompatibility antigens referred to as mls (minor lymphocyte stimulating). Thus, there are numerous proteins present on the cell surface of different types of cells, which designate the nature of the host. Because of these differences, when administering allogeneic cells or transplanting allogeneic tissue, one frequently encounters rejection.

In order to avoid the rejection by the immune system, the patient is normally treated systemically with immunosuppressive drugs. These drugs have the effect of inhibiting all or a substantial proportion of the immune system associated with the rejection of the foreign cells and tissue. The immunosuppressive drugs, are for the most part, highly toxic and can leave the person debilitated and susceptible to pathogenic organisms. However, in many instances, the life-threatening nature of the need for the foreign cells or tissue is sufficiently great, so as to warrant the extreme nature of the allogeneic transplant. Since in many instances, treatment with autologous cells or tissues is not available, there is substantial interest in being able to find alternative therapies, which will allow for the administering of allogeneic cells, without the concomitant heavy immunosuppression of the patient.

RELEVANT LITERATURE

Kosugi and Shearer, *J. Immunol.* (1991) 146:1416–1421 describe the effects of cyclosporin A on generation of natural killer (NK) cells. Almartine et al, *Transplantation* (1990) 50:969–973 studied the effect of immunosuppressive regimens with renal transplant recipients. Bix et al, *Nature* (1991) 349:329–331 describe rejection of syngeneic $\beta$2-microglobulin deficient bone marrow cells by NK1.1$^+$ cells. Laio et al, *Science* (1991) 253:199–201 report that T-cell blasts from MHC Class I deficient mutant mice serve as target cells for NK cells in vitro. Ohlan et al, *Science* (1989) 246:666–667 report that rejection of bone marrow grafts in irradiated mice is mediated by NK cells and controlled by genes linked to the major histocompatibility complex.

SUMMARY OF THE INVENTION

The subject invention concerns the use of compositions for therapies, where the compositions comprise genetically-modified cells employed in conjunction with immunosuppressive agents, where the immunosuppressive regimen is substantially diminished from a normal regimen to avoid its inherent toxicity or other physiological adverse characteristics, where in the normal regimen genetically unmodified but foreign cells are administered to the host. Usually, the genetic modification will be in a gene product associated with immune recognition by the host and/or enhancement of therapeutic capacity and depending upon the nature of the genetically modified cells, particular immunosuppressive agents or regimens may be preferred.

DESCRIPTION OF THE SPECIFIC EMBODIMENTS

Regimens are provided, as well as compositions, for various cellular therapies, where the regimens invoke genetically modified cells in conjunction with an immunosuppressive agent, where the immunosuppressive agent is used in a milder regimen than is normally associated with cellular or organ transplant therapies involving foreign, particularly allogenic cells or organ transplants. The immunosuppressive agent provides for a reduction in the population and/or activity of the effector cells of the host immune system. The reduced response of the immune system to the allogeneic cells is evidenced by the reduced immunosuppressive regimen required for maintenance of the modified cells as compared to the unmodified cells.

One or more genetic modifications may be present, where the genetic modification may be an insertion, deletion or combination thereof, e.g. substitution. Of interest are genetic modifications which reduce the expression of one or more different protein antigens associated with immune recognition of said allogeneic cells. One genetic modification will result in a reduction in the level of at least one major histocompatibility complex antigen, Class I, II, particularly I. More particularly, the genetic modification may result in a substantial diminution of all of the Class I antigens, that is, Class I-A, -B, and -C, particularly HLA antigens for humans. The genetic modification may be the result of knocking out of a specific gene, changing its regulatory response, introduction of a construct which inhibits expression of a target gene, such as a ribozyme or antisense gene, introduction of a gene which inhibits transport of a target gene, where the target gene is normally transported to the cell surface, e.g. a dysfunctional $\beta$2-microglobulin gene, and the like.

In addition to a gene directly involved with the immune system, other genetic modifications include introduction of capabilities for producing a wide variety of proteins, which may be naturally occurring, such as: hormones, e.g., insulin, growth hormone, luteinizing hormone, and the like; clotting factors, e.g., Factor VIIIc or -vW, Factor IX, etc.; cytokines e.g., interleukins 1–11; other factors associated with hematopoiesis, e.g., colony stimulating factors such as G, M and GM, erythropoietin; growth factors e.g., growth factor, nerve growth factors, platelet derived growth factor, bone morphogenetic or growth factors; miscellaneous factors such as tumor necrosis factor, and the like.

Besides the above genetic capabilities which may be introduced into the cells, other capabilities which are more directed to disease states, include protection of the cell from infection from, for example, HIV, HTLV-I and II, hepatitis A, B, or C virus, influenza virus, enteroviruses e.g., EBV, rhinoviruses, etc.; alteration of cell surface receptors which allow targeting or homing to sites of malignant, infectious or inflammatory diseases including homing receptors, growth factor or cytokine receptors, antigen receptors such as T cell receptors, B cell receptors and the like.

For adding capabilities, one may introduce a construct comprising the gene of interest with appropriate transcriptional and translational regulatory regions. Using homologous recombination, one may modify the transcriptional initiation regulatory region by insertion of an enhancer, changing the promoter region to a different promoter, e.g. stronger, constitutive as distinct from inducible, etc., insert an amplifiable gene in proximity to the target gene, knock out or introduce a gene for a regulatory promoter, which provides the desired level of expression of the gene of interest, and the like.

Depending upon the nature of the genetic modification, either homologous recombination or illegitimate recombination may be involved. Various techniques exist for homologous recombination; see, for example, Kucherlapati et al, *Mol. Cell. Bio.* 5:714–720, 1985; Thomas and Capecchi, *Cell* 51:503–512, 1987; Nandi et al, *PNAS USA* 85:3845–3849, 1988; Mansour et al, *Nature* 336:348–352, 1988; Thompson et al, *Cell* 56:316–321, 1989; and Joynet et al, *Nature* 338:153–156, 1989.

For homologous recombination, a DNA construct will be employed which comprises at least a portion of the locus into which the construct is to be integrated. The homologous sequence will normally include at least about 100 bp, preferably at least about 150 bp, more preferably at least about 300 bp of the target sequence and not exceeding 2000 kbp, usually not exceeding 20 kbp, being preferably less than about a total of 10 kbp. Where an insertion or deletion is involved, usually there will be at least about 50 bp of homology on both sides of the insertion or deletion, in order to provide for double cross-over recombination. Either insertional (O type) or replacement (Ω type) constructs may be employed.

Upstream and/or downstream from the target gene construct may be a gene which provides for identification of whether a double cross-over has occurred. For this purpose, the herpes simplex virus thymidine kinase simplex gene may be employed, since the presence of the thymidine kinase gene may be detected by the use of nucleoside analogs, such as acyclovir or gancyclovir, for their cytotoxic effects on cells that contain a functional HSV-tk gene. The absence of sensitivity to these nucleoside analogs indicates the absence of the thymidine kinase gene and, therefore, where homologous recombination has occurred, that a double cross-over event has also occurred.

The presence of a selectable marker gene (i.e. neomycin resistance, hygromycin resistance, or a marker providing for detection by screening, e.g. a protein, such as β-galactosidase or a surface marker) inserted into the target locus establishes the integration of the target construct into the host genome. However, DNA analysis will be required in order to establish whether homologous or non-homologous recombination occurred. This can be determined by employing a hybridization probe specific for sequences just beyond the ends of the targeting vector to identify the appropriate novel restriction fragment created by the homologous recombination event.

The polymerase chain reaction may be used with advantage in detecting the presence of homologous recombination. Primers may be used which are complementary to a sequence within the construct and complementary to a sequence outside the construct and at the target locus. In this way one can obtain DNA duplexes having both of the primers present in the complementary chains if homologous recombination has occurred. By demonstrating the presence of the primer sequences or the expected size sequence, the occurrence of homologous recombination is supported.

The construct may further include a replication system which is functional in the mammalian host cell. For the most part, these replication systems will involve viral replication systems, such as Simian Virus 40, Epstein-Barr virus, papilloma virus, adenovirus and the like.

When a marker gene is involved, as an insert, and/or flanking gene, depending upon the nature of the gene, it may have the wild-type transcriptional regulatory regions, particularly the transcriptional initiation regulatory region or a different transcriptional initiation region. Whenever a gene is from a host where the transcriptional initiation region is not recognized by the transcriptional machinery of the mammalian host cell, a different transcriptional initiation region will be required. This region may be constitutive or inducible. A wide variety of transcriptional initiation regions have been isolated and used with different genes. Of particular interest as promoters are the promoters of metallothionein-I and II from a mammalian host, thymidine kinase, β-actin, immunoglobulin promoter, human cytomegalovirus promoters, and SV40 promoters. In addition to the promoter, the wildtype enhancer may be present or an enhancer from a different gene may be joined to the promoter region.

The construct may further include a replication system for prokaryotes, particularly *E. coli*, for use in preparing the construct, cloning after each manipulation, allowing for analysis, such as restriction mapping or sequencing, followed by expansion of a clone and isolation of the plasmid for further manipulation. When necessary, a different marker may be employed for detecting bacterial transformants.

Once the vector has been prepared, it may be further manipulated by deletion of the bacterial sequences as well as linearization. In the case of the O-type vector, a short deletion may be provided in the homologous sequence, generally not exceeding about 500 bp, generally being from about 50 to 300 bp.

Once the construct has been prepared and manipulated and the undesired sequences removed from the vector, e.g., the undesired bacterial sequences, the DNA construct is now ready to be introduced into the target cells. As already indicated, any convenient technique for introducing the DNA into the target cells may be employed. After genetic modification e.g., transfection of the target cells, the target cells may be selected by means of positive and/or negative markers, as previously indicated, neomycin, acyclovir, gancyclovir resistance, etc. Those cells which show the desired phenotype may then be further analyzed by restriction analysis, electrophoresis, Southern analysis, polymerase chain reaction, or the like. By identifying fragments which show the presence of the lesion(s) at the target gene site, one can identify cells in which homologous recombination has occurred.

Of interest is the inactivation of at least one, preferably both, copies of a subunit of an MHC antigen, more particularly, β2-microglobulin. That is, of interest are methods which provide for cells lacking at least one MHC antigen, Class I or Class II, preferably Class I, which cells may serve a variety of functions in a viable host. The method involves transfection of mammalian cells, particularly normal cells, of a predetermined species with DNA associated with one of the loci related to the major histocompatability complex antigen subunits: the β2-microglobulin gene, the α-subunit(s) of the Class I or II MHC antigens or the β-subunit(s) of the Class II MHC antigens, other molecules involved in antigen presentation, e.g. peptide transporters, such as ham1 and -2 or induction of MHC expression, e.g. IFN gamma receptor. Also of interest are genes encoding factors that act in trans in the regulation of the MHC antigens, e.g. transcription factors, and, in particular, dominant negative mutations thereof. The human Class II MHC antigens are HLA-DR, DP and DQ, where DR is of primary interest.

The DNA will comprise at least a portion of the gene(s) at the particular locus with introduction of a lesion into at least one, usually both copies, of the native gene(s), so as to prevent expression of a functional MHC antigen molecule. The lesion may be an insertion, deletion, replacement or combination thereof. When the lesion is introduced into only one copy of the gene being inactivated, the cells having a single unmutated copy of the target gene are amplified and may be subjected to a second DNA modification, where the lesion may be the same or different from the first lesion, usually different, and where a deletion, or replacement is involved, may be overlapping at least a portion of the lesion originally introduced. The resulting modified cells are screened for the absence of a functional target antigen and the DNA of the cell may be further screened to ensure the absence of a wild-type target gene. Alternatively, a homozygous mutant may spontaneously occur and the cells may be screened for this event using appropriate labels, e.g. antibodies for the MHC antigen(s).

The MHC antigen deficient cells will be selected to achieve a particular function and be introduced into a mammalian host or used for research or other purpose. Also of interest will be the stem cells which act as the progenitors for any of the above cells, which may be the original progenitor or a progenitor cell which is already dedicated to a particular lineage. Of particular interest will be epidermal cells, such as keratinocytes, retinal epithelial cells, endothelial cells, myoblasts, hematopoietic cells, glial and neuronal cells, and other cells which may be readily manipulated in vitro, maintained for long periods of time in culture and may be introduced into a host, where the cells will remain viable and functional for long periods of time.

The procedures employed for inactivating one or both copies of a particular MHC antigen will be similar, differing primarily in the choice of sequence, selectable marker used, and the method used to identify the absence of the MHC antigen, although similar methods may be used to ensure the absence of expression of a particular antigen. Since the procedures are analogous, the inactivation of the β2-microglobulin gene will be used as exemplary. It is to be understood that substantially the same procedures, but with other genetic sequences, will suffice fort he α-subunits of the Class I MHC antigens and for the α- and β-subunits of the Class II MHC antigens, as well as relevant trans acting sequences.

The homologous sequence for targeting the construct may have one or more deletions, insertions, substitution or combinations thereof. For example, the β2-microglobulin targeting vector may or may not include a deletion at one site and an insertion at another site, which includes a gene which may be used for selection, where the presence of the inserted gene will result in a defective inactive protein product. Preferably, substitutions are employed. For an inserted gene, of particular interest is a gene which provides a marker, e.g., antibiotic resistance such as neomycin resistance, including G418 resistance, hygromycin resistance, etc.

DNA constructs may be employed which provide for the desired introduction of the lesion into the cell. The constructs may be modified to include functional entities other than the mutated sequence which may find use in the preparation of the construct, amplification, transformation of the host cell, and integration of the construct into the host cell. Techniques which may be used include calcium phosphate/DNA coprecipitates, microinjection of DNA into the nucleus, electroporation, bacterial protoplast fusion with intact cells, transfection, lipofection, or the like. The DNA may be single or double stranded, linear or circular, relaxed or supercoiled DNA. For various techniques for transforming mammalian cells, see Keown et al., *Methods in Enzymology* (1990) 185:527–537.

The deletion will be at least about 1 bp, more usually at least about 10 bp, and generally not more than about 20 kbp, where the deletion will normally include at least a portion of the coding region including a portion of or one or more exons, a portion of or one or more introns, and may or may not include a portion of the flanking non-coding regions, particularly the 5'-non-coding region (transcriptional regulatory region). Thus, the homologous region may extend beyond the coding region into the 5'-non-coding region or alternatively into the 3'-non-coding region. Insertions will generally not exceed 10 kbp, usually not exceed 5 kbp, generally being at least 50 bp, more usually at least 200 bp.

Genetic modification of the cells in which one of the copies has been inactivated may then be performed in the same or different way from the previous method of genetic modification. The resulting genetically modified cells may then be selected by the absence of the target MHC antigen on the surface of the cell. This can be achieved in a variety of ways. For example, one may use antibodies to any epitope of the target MHC antigen in conjunction with complement to kill any cells having the antigen. Alternatively, one may use conjugates of the appropriate antibody, particularly monoclonal antibody with a toxin, such as the A chain of ricin, abrin, diphtheria toxin, or the like. One may select using a FACS employing fluorescent labeled antibodies for the target antigens. Affinity chromatography may be employed, where antibodies may be used to remove cells expressing the target antigen. The resulting cells which survive should be at least substantially free of at least one MHC antigen on their surface and not be as subject to transplant rejection when introduced in vivo, as compared to wild-type cells.

The cells which may be subjected to genetic modification may be any mammalian cells of interest, which may find use in cell therapy, research, interaction with other cells in vitro or the like. Cell of particular interest include, among other lineages, the islets of Langerhans, adrenal medulla cells which may secrete dopamine, osteoblasts, osteoclasts, epithelial cells, endothelial cells, T-lymphocytes, neurons, glial cells, ganglion cells, retinal cells, liver cells, bone marrow cells, and myoblast (muscle) cells.

Alternatively, cells from bare lymphocyte syndrome patients may be isolated in accordance with conventional ways, e.g., panning, affinity columns, magnetic beads, or the like. By employing monoclonal antibodies specific for the lymphoid cell type, B- or T-cell, using monoclonal antibodies for such markers as CD 3, 4, 8, 10, 15 or 19, the desired group of cells and their progenitors may be isolated in a substantially homogeneous composition. The genetically defective cells may be used in the same manner as MHC antigen defective cells produced by homologous recombination.

The cells which have been modified will normally be screened to ensure that the cells have the desired genetic modification at an appropriate site to provide for the appropriate phenotype. The cells may be grown in an appropriate nutrient medium for expansion and used in a variety of ways. For example, with keratinocytes, the cells may be used for replacement of skin in the case of burns, where keratinocytes may be grown to form multiple continuous layers prior to application. Similarly, the keratinocytes may be used in the case of plastic surgery to replace skin removed from the host for use at another site. Other uses for the keratinocytes include transplantation in decubitus ulcers.

In the case of islets of Langerhans, they may be grown and introduced into capsules or otherwise for insertion into a host for the production of insulin. In the case of retinal epithelial cells, they may be injected into the subretinal space of the eye to treat visual disorders, such as macular degeneration. In the case of immune cells, they may be injected into the bloodstream or elsewhere to treat immune deficiency or to augment immunity. In the case of myoblasts, they may be injected at various sites to treat muscle wasting diseases, such as Duchenne muscular dystrophy. In the case of cells genetically modified for other purposes, for example, to produce therapeutic compounds, to target malignant or infectious disease processes, or to be resistant to pathogens, similar methods of administration will be employed.

The genetically modified cells may be administered as dispersed cells, as cells grown in culture, for example, on a support, where the cells may form a continuous layer or plurality of layers on a physiologically acceptable support, may be provided as tissue, where only a portion of the targeted cells have been modified, usually at least about 5%, preferably at least about 10%, and may be as high as 15% or more. In many situations, it may be sufficient to provide genetically dispersed cells to the host, particularly at the site where the cells are intended to function. For example, genetically modified islets of Langerhans may be injected into the pancreas. The manner of administration will vary widely, depending upon the nature of the cells, the form in which the cells are administered, the nature of the disease, and the like. For treatment of skin burns, one would normally apply a layer of keratinocytes, by themselves or in conjunction with other cutaneous cells, where the cells may be supported by a physiologically acceptable support, such as a layer of collagen, collagen coated fabric, fabric, or the like. Other conditions and the manner of administration are illustrated by the following: muscle wasting diseases, such as muscular dystrophy, where the cells are injected directly into affected muscles in the extremities or other sites; endocrine disorders, such as diabetes or growth hormone deficiency, where the cells may be injected into subcutaneous sites directly or in various capsules or hollow fibers; hepatic injury or infection, by injection of the cells into the liver; degenerative diseases of the retina, where the cells are injected subretinally; malignancies or infections, where cells of the immune system, including cytotoxic lymphocytes, monocytes or other leukocyte populations or subpopulations, may be injected into the blood stream body cavities, such as the abdominal cavity, pleura, sinuses, respiratory tract or bladder. The leukocytes may have been previously modified or selected to have greater specificity against malignancies, such as lymphomas, leukemias, melanomas, breast cancer, lung cancer, other carcinomas and sarcomas; or against infections, such as those due to HIV, HTLV, CMV, papilloma virus, Pneumococcus, Legionnaires disease, Salmonella, Pseudomonas, etc.

The immunosuppressive regimen may take many forms and may be combinations of forms. Immunosuppressive regimens include irradiation, chemotherapy, specific immunosuppressive agents, and the like. Of particular interest are immunosuppressive agents, such as cyclosporin A, azathioprine, FK-506, corticosteroids, e.g., prednisolone and methylprednisolone, monoclonal antibodies against various surface membrane proteins of the lymphoid and/or myeloid lineage, etc. For example, one may use monoclonal antibodies which are conjugated with a toxin and directed against the T cell receptor, the surface membrane proteins CD3, 4, 5, 7, 8, 45 and 69 and the like; IL-2 receptor, other interleukin receptors, and the like. One may also use highly specific immunosuppressive agents which are directed against antigen specific receptors or cytotoxic lymphocytes responsible for the rejection of transplanted cells or tissue, where such receptors are part of the recognition triad consisting of the T cell receptor, the antigenic fragment and the MHC molecule.

The level of immunosuppressive regimen which is employed with the modified cells, will be substantially less rigorous than would normally be used in a comparable treatment with unmodified cells. The amount of immunosuppression required for maintenance of the modified cells will vary depending upon the nature of the match between the donor and recipient cells, the level of activity of the host's immune system, the particular site at which the foreign cells are introduced, and the type and number of transplanted cells. The regimens which can be employed may be based on existing or newly developed regimens associated with the transplantation of foreign, e.g., allogeneic, tissue. Therefore, the dosage level, frequency of administration, manner of administration and formulations for different situations and patients will have been established. The subject invention provides for reduction in the adverse effects of these regimens, where the reduction may be as a result of lower dosages, reduced frequency of administration, delaying the initiation of administration of the drug, or combinations thereof. The reduced therapy may approach or reach the initiation of rejection, which may be evidenced by a significant increase in activated cells of the immune system, signs of necrosis, withdrawal of the graft tissue from the endogenous tissue, and the like. The therapy can be maintained to prevent initiation of rejection by monitoring the transplant and/or immune system and regulating the administration of the immunosuppressive agent to maintain the graft at or preferably below initiation of rejection.

The immunosuppressive agents may have greater or lesser specificity for a lineage or subpopulation of leukocytes. In selecting the immunosuppressive agent one would consider the nature of the cells associated with the rejection and select an agent(s) which is effective in suppressing such population. Since in many cases, different subpopulations may be associated with rejection at particular body sites, knowledge of the populations involved and the selectivity of the agent will help in selecting the agent and the mode of administration. For example, antibodies may be employed which are selective for T cells or subsets of T cells, e.g. $CD4^+$, $CD8^+$, $CD69^+$, etc.

Alternately as is frequently practiced today, one may wish to initially use a level comparable to or somewhat less than what would normally be used as the initial level or administration and then rapidly reduce the level of administration to not more than 75% of the original level, preferably not more than about 60% of the original level. Frequently levels of 50% or less may be obtainable.

While there may be enormous variation in the combination of immunosuppressive agents and administration of genetically modified cells, and no reasonable ranges can be suggested for all the applicable situations, the example described below indicates a significant reduction in the immunosuppressive agents dosage required to prolong transplant survival.

Diseases or disease states which may be treated by the subject cells include skin trauma or ulcers, burns, neoplasia, infections due to viruses, particularly in an immunodeficiency setting, muscle wasting syndrome, endocrine disorders due to insulin or growth hormone deficiency, hepatic injury or infection, degenerative diseases of the eye, such as macular degeneration or retinitis pigmentosa, etc. or the nervous system, such as Parkinson's disease, Alzheimer's disease, etc.

The subject methodology may be enhanced by providing for kits which provide the various components of the methodology. That is, one may provide for cells in conjunction with the appropriate immunosuppressive agent, with labeling indicating the manner of administration of the immunosuppressive agent. Other components of the kits may include surgical or injection equipment applicable to administration of the cells or tissue and drugs.

The following examples are offered by way of illustration, not by way of limitation.

EXPERIMENTAL

The technique described by Billingham and Medawar, *J. Exp. Biol.* 28:385 (1951), is employed. Donor mice with skin largely in the resting phase of the hair growth cycle are selected. To prepare the skin grafts, donor mice are euthanized and shaved both ventrally and dorsally. The skin is washed with cotton drenched in 70% alcohol. Pinch grafts are removed by grasping the skin with fine forceps and lifting up to create a small "tent". With a curved (#12) scalpel blade, skin is removed about 10 mm below the tip of the tent. The graft is placed dermis down on filter paper in a petri dish. Pinch grafts are removed in an anterior-posterior direction, removing one row of pinch grafts at a time. A typical adult donor mouse can provide up to 13 body skin grafts.

The pinch grafts, are scraped clean before transplantation. One edge of the graft is grasped with straight fine forceps and with small firm strokes of the #15 scalpel blade, and the subcutaneous connective tissue is removed. A reasonable amount of pressure is required to remove the connective tissue. When the graft is fully scraped, it is placed, dermis-side down, on moistened filter paper.

The recipient mouse is then anesthetized with ether or avertin and immobilized. The upper lateral side of the animal is shaved with two short strokes of the electric shaver (against the grain of the hair) and the skin is prepped with 70% alcohol. To prepare the graft bed, a small strip of skin is removed with curved scissors, held horizontally, right on top of the lateral rib cage. The underlying panniculus carnosus and blood vessels are left intact. A piece of skin about the same size and shape as the prospective transplant is removed. The donor graft is then placed in the graft in the bed maintaining sterile technique. The transplant should be positioned so that the new hair will grow in the opposite direction to that of the recipient. This will make it easier to locate the transplant when the donor and recipient animals have similar hair color. The graft should be cut to fit precisely in the graft bed.

The graft is then covered with a piece of vaseline impregnated tulle and a plaster of paris cast is placed around the thorax of the mouse. The bandage should be tight enough to prevent slipping of the graft, but loose enough to allow full respiration. When the plaster has dried, the recipient mice are returned to their cages. The mice are observed daily.

In order to detect a first set rejection the bandages are removed after 7–9 days. The animals are lightly anesthetized with ether or avertin. With a bandage shear, the plaster bandage cast is removed while keeping the dressing attached to the bed. The graft is evaluated and the animal is then returned to its cage.

Evaluation of Skin Grafts

Grafts transplanted onto immunologically naive mice are rejected according to a "first set" rejection response. This response usually takes from 10–13 days for allo- and xenografts, depending on the histoincompatibility. A syngeneic graft from male donor into female recipient may take up to 7 weeks to be rejected, but in some strains female recipients never reject a syngeneic graft from a male donor.

If the animal has been previously exposed to the particular histocompatibility antigen, it will reject the graft faster than 10 days. This is called a "second set" rejection response.

A graft which is to be rejected shortly after removal of the bandage, will often have a "glistening" appearance. Such grafts often become a full scab within 12 hours. These grafts are often on mice which have been presensitized (second set response) or can mount an unusually strong immune response. Mice which reject the skin graft according to a first set response show grafts which are healing in nicely during the first 1–2 days after removal of the bandage. Graft rejection usually starts by scab formation in one corner. The scab spreads and the whole graft becomes a scab in 1–2 days. Grafts that are accepted by the mice continue to heal and do not show any scab formation. After wound healing is complete, hair will start growing on the graft, in the same or opposite direction, depending on whether the direction of the skin graft has been reversed.

Mice can also reject their grafts slowly by "chronic" rejection. This rejection pattern is usually expressed as a gradual decrease in the size of the graft, sometimes accompanied by hair loss on the graft. It can take several months, or as long as a year, for the graft to disappear entirely.

In the case of the C57Bl/6×129 mice who were recipients of skin transplants, consisting of flank or lateral skin tissue from 129 donors, in the presence or absence of any immunosuppressive agent, there was no sign of rejection. In the case of B10.BR mice who were the recipients of grafts from either 129 or β2-microglobulin-deficient mice (Koller et al., *Science* (1990) 248:1227–1230; Koller and Smithies, *PNAS USA* (1989) 86:8932–8935) when the mice were given 2 mg of cyclosporin A daily, there was no sign of rejection.

However, where the same B10.BR mice were recipients of grafts from the same two donor strains, and only 200 µg of cyclosporin daily was provided, rejection occurred between days 15 to 18 with 129 donors. In contrast, rejection occurred between days 20 to 30 with the β2-microglobulin deficient mice as donors with the same treatment regimen.

In another experiment, a range of concentrations were employed where B10.BR was the recipient mouse and β2-microglobulin-deficient the donor mouse, where the concentrations of cyclosporin A ranged from 0 to 700 µg; below 200 µg, all of the mice had lost the graft by day 20 while at 200 µg and above, the mice retained the graft for at least 25 days.

The following table summarizes these results.

TABLE I

TIME OF SKIN GRAFT REJECTION BY B10.BR (H-2$^K$) RECIPIENT

| Cyclosporin A Dose | 129 Donor | β2$^-$ Donor* |
|---|---|---|
| 0 | 9.5 days | 9.25 days |
| 70 µg | 10.5 days | 15.25 days |
| 200 µg | 16.75 days | 25.25 days |
| 700 µg | 15 days | 28 days |
| 2 mg | no rejection | no rejection |

(N = 4 per group)
*β2$^-$- β2-microglobulin deficient

It is evident from the above results, that the subject method provides for substantial advantages. By using genetically modified cells, particularly cells which have been modified in such a way as to reduce the available MHC antigens on the surface which are different from the recipient receiving a graft, one can provide for substantially reduced immunosuppressive regimens. Thus, the individual will be able to receive the graft, while still retaining sufficient defense mechanisms, so as to have a more positive outcome and be less susceptible to infection. In addition, one can avoid the many adverse side effects of many of the immunosuppressive regimens, so that the individual is not only healthier during the treatment, but is healthier after the treatment, as well.

All publications and patent applications mentioned in this specification are indicative of the level of skill of those skilled in the art to which this invention pertains. All publications and patent applications re herein incorporated by reference to the same extent as if each individual publication or patent application was specifically and individually indicted to be incorporated by reference.

Although the foregoing invention has been described in some detail by way of illustration and example for purposes of clarity of understanding, it will be understood that certain changes and modifications may be practiced within the scope of the appended claims.

What is claimed is:

1. A method of prolonging graft acceptance, the method comprising:

administering to a mammalian host a graft comprising genetically modified allogeneic skin cells, said genetic modification being a result of recombination with a DNA construct resulting in inactivation of expression of β2-microglobulin; and a diminished regimen of an immunosuppressive therapy comprising administration of an immunosuppressive drug, said drug being selected from the group consisting of cyclosporin and FK-506, wherein the regimen necessary to maintain said graft at or below initiation of rejection of said genetically modified allogeneic cells is diminished as compared to the regimen for cells lacking such genetic modification.

2. A method according to claim 1, wherein said skin cells are cells dispersed in a medium.

3. A method according to claim 1, wherein said skin cells are contiguous tissue forming cells.

4. A method according to claim 1, wherein said skin cells are keratinocytes.

5. A kit for transplanting skin cells to a mammalian host, said kit comprising:

genetically modified allogeneic skin cells, wherein said genetic modification is a result of recombination with a DNA construct resulting in inactivation of expression of β2-microglobulin; and a drug capable of suppresing the population or activity of cells of said host associated with rejection of said allogeneic cells said drug being selected from the group consisting of cyclosporine A and FK-506.

6. A kit according to claim 5, further including surgical or injection devices for administering at least one of said cells and said drug.

* * * * *